United States Patent
Koehler et al.

(10) Patent No.: US 11,964,022 B2
(45) Date of Patent: Apr. 23, 2024

(54) SMALL MOLECULE BINDERS OF THE ONCOGENIC FUSION TRANSCRIPTION FACTOR PAX3-FOXO1

(71) Applicants: Massachusetts Institute of Technology, Cambridge, MA (US); Universität Zürich, Zürich (CH)

(72) Inventors: Angela Nicole Koehler, Belmont, MA (US); Shelby Doyle, Cambridge, MA (US); Becky Leifer, Malden, MA (US); Madeleine Henley, Brighton, MA (US); Beat W. Schaefer, Zürich (CH); Marco Wachtel, Zürich (CH)

(73) Assignees: Massachusetts Institute of Technology, Cambridge, MA (US); Universität Zürich, Zürich (CH)

( * ) Notice: Subject to any disclaimer, the term of this patent is extended or adjusted under 35 U.S.C. 154(b) by 0 days.

(21) Appl. No.: 17/946,898

(22) Filed: Sep. 16, 2022

(65) Prior Publication Data
US 2023/0149552 A1    May 18, 2023

Related U.S. Application Data

(60) Provisional application No. 63/280,091, filed on Nov. 16, 2021.

(51) Int. Cl.
*A61K 47/55* (2017.01)
(52) U.S. Cl.
CPC .................... *A61K 47/55* (2017.08)
(58) Field of Classification Search
CPC ...................................... A61K 47/55
See application file for complete search history.

(56) References Cited

U.S. PATENT DOCUMENTS 8,304,521 B2    11/2012  Hollenbach et al.

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Martin, et al., (2013) "Cell-Based Small-Molecule Compound Screen Identifies Fenretinide as Potential Therapeutic for Translocation-Positive Rhabdomyosarcoma", Plos One, vol. 8(1), Article e55072, pp. 1-12; abstract, p. 2, Figure 1.
Jothi, et al., (2013) "Small Molecule Inhibition of PAX3-FOXO1 Through AKT Activation Suppresses Malignant Phenotypes of Alveolar Rhabdomyosarcoma", mol Cancer Ther., vol. 12(12), pp. 1-19; doi: 10.1158/1535-7163. MCT-13-0277, abstract; p. 6, para 4 to p. 7, para 1; p. 13, Figure 1A.
PUBCHEM-SID: 160950271 Deposit Date: Mar. 4, 2013 (Mar. 4, 2013) pp. 1-5; p. 2.

* cited by examiner

*Primary Examiner* — Nizal S Chandrakumar
(74) *Attorney, Agent, or Firm* — McDonnell Boehnen Hulbert & Berghoff LLP

(57) ABSTRACT

The present disclosure provides compounds having the general formula P-L-U, or pharmaceutically acceptable salts thereof, wherein P is a FOXO1 fusion protein binding moiety, L is a bivalent linker, and U is an ubiquitin ligase binding moiety. Also provided are pharmaceutical compositions containing such compounds and methods of using such compounds.

5 Claims, 10 Drawing Sheets

KI-P3F-032 Photo-O

SMALL MOLECULE BINDERS OF THE ONCOGENIC FUSION TRANSCRIPTION FACTOR PAX3-FOXO1

CROSS REFERENCE TO RELATED APPLICATIONS

This application claims priority to U.S. Provisional Application No. 63/280,091, filed Nov. 16, 2021, the contents of which are herein incorporated by reference in their entirety.

FEDERAL FUNDING STATEMENT

This invention was made with government support under CA231630 awarded by the National Institutes of Health. The government has certain rights in the invention.

BACKGROUND OF THE INVENTION

Fusion-positive rhabdomyosarcoma (FP-RMS) is a devastating childhood cancer that is marked by poor survival rates and resistance to chemotherapy. The majority (~60%) of FP-RMS cases are driven by a fusion between the transcription factors paired box 3 (PAX3) and forkhead box 01 (FOXO1) (forming PAX3-FOXO1), which as a fusion transcription factor acts to lock cells in a myogenic state and promotes excessive growth as well as migration to other organs. A clear way to target this disease is to inhibit the function of PAX3-FOXO1, however, because PAX3-FOXO1 is considered a prototypical "undruggable" transcription factor, essentially no progress towards this goal has been reported to date.

SUMMARY OF THE INVENTION

In a first aspect, the disclosure provides a compound of Formula I:

$$P-L-U \quad (I)$$

or a pharmaceutically acceptable salt thereof, wherein
P is a FOXO1 fusion protein binding moiety;
L is a bivalent ligand; and
U is an ubiquitin ligase binding moiety.

In one embodiment of the first aspect, the disclosure provides a compound where in P is of Formula II:

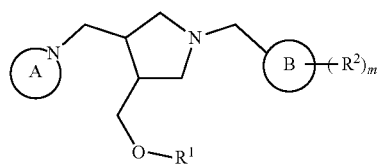

(II)

wherein
m is an integer 0, 1, or 2;
ring A represents a 6- or 7-member heterocyclyl optionally substituted with one or two $R^3$;
ring B represents an aryl, heteroaryl, heterocyclyl, or $C_4$-$C_8$ cycloalkyl;
$R^1$ is hydrogen, $C_1$-$C_6$ alkyl, $C_1$-$C_6$ haloalkyl, or a bond to L; and
each $R^2$ is independently halogen, —$NO_2$, —CN, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, aryl optionally substituted with one or more $R^4$, heteroaryl optionally substituted with one or more $R^4$, heterocyclyl optionally substituted with one or two $R^5$, or $C_4$-$C_8$ cycloalkyl optionally substituted with one or more $R^5$, or $R^2$ is a bond to L provided that only one bond to L is present in P;
where
each $R^3$ is independently selected from halogen, —$NO_2$, —CN, $C_1$—C alkyl, $C_1$—C haloalkyl, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy, or $R^3$ groups when attached to the same carbon atom form =O;
each $R^4$ is independently selected from halogen, —$NO_2$, —CN, $C_1$—C alkyl, $C_1$—C haloalkyl, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy;
each $R^5$ is independently selected from halogen, —$NO_2$, —CN, $C_1$—C alkyl, $C_1$—C haloalkyl, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy, or $R^5$ groups when attached to the same carbon atom form =O.

In a second aspect, the disclosure provides a pharmaceutical composition comprising a compound of the first aspect of the disclosure and pharmaceutically acceptable carrier, solvent, adjuvant or diluent.

In a third aspect, the disclosure provides a method of treating cancer comprising administering to a subject in need of such treatment one or more compounds according the first aspect of the disclosure or a pharmaceutical composition according to the second aspect of the disclosure.

In a fourth aspect, the disclosure provide a compound according to the first aspect of the disclosure or a pharmaceutical composition of the second aspect of the disclosure for treating rhabdomyosarcoma.

In a fifth aspect, the disclosure provides a method of ubiquitinating a PAX3-FOXO1 fusion protein in a cell, comprising administering one or more compounds according the first aspect of the disclosure or a pharmaceutical composition according to the second aspect of the disclosure to the cell.

BRIEF DESCRIPTION OF THE DRAWINGS

FIG. 1A: KI-P3F-032-based PROTACs are synthesized to contain different flexible linker sizes, E3 ligase binders, and linker attachment points (shaded ovals). FIG. 1B shows the general synthetic approach for rapidly synthesizing libraries of KI-P3F-032-based PROTACs.

FIG. 2A shows how ligand-protein interactions are detected using SMMs. FIG. 2B shows data from pilot screen of FLAG-tagged PAX3-FOXO1 overexpressed in HEK293T lysates.

FIG. 3A provides the structure of KI-P3F-032. FIG. 3B shows CETSA data comparing melting of PAX3-FOXO1 and FOXO1 (using an antibody that is targeted to the C-terminus of FOXO1) in the presence and absence of KI-P3F-032. FIG. 3C shows luciferase reporter data indicating that KI-P3F-032 does not significantly affect the function of PAX3-FOXO1.

FIG. 4A shows PAL experiments that show that upon UV irradiation, bands corresponding to the molecular weights of PAX3-FOXO1 and FOXO1 are detected (biotin detection via fluorescently labeled streptavidin). Samples were also affinity purified using streptavidin resin. FIG. 4B shows samples from the same experiment that were instead subjected to western blots using an antibody targeted to the C-terminus of FOXO1. FIG. 4C shows the structure of the photoprobe.

DETAILED DESCRIPTION OF THE INVENTION

Figure 1A:
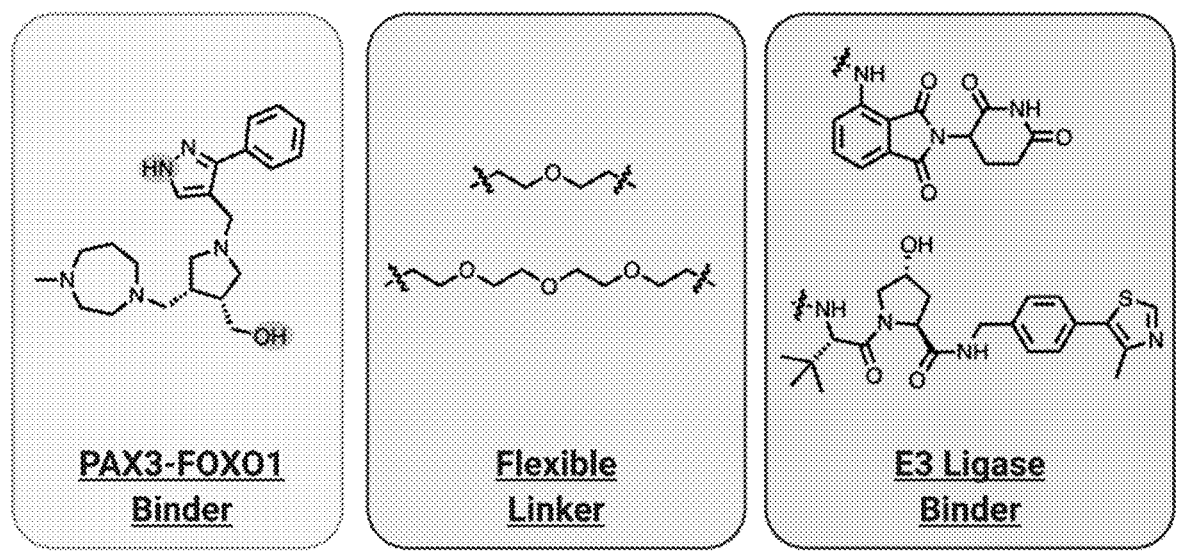
FIG. 1A and FIG. 1B depict the general synthetic approach to prepare the compounds of the disclosure.

The inventors have discovered and validated a drug-like small molecule that directly binds to PAX3-FOXO1 but does not affect its function. This ligand has been developed as a handle for bifunctional proximity-inducing strategies, specifically to develop a proteolysis-targeting chimaera (PROTAC) degrader of PAX3-FOXO1. Such a PAX3-FOXO1 PROTAC may be used for the treatment of cancers such as FP-RMS, opening the door for the first new treatments for this disease in decades. In particular, the inventors have discovered the utility of KI-P3F-032 as a ligand for PAX3-FOXO1 proteolysis targeting chimaeras (PROTACs).

Definitions

The following terms and expressions used herein have the indicated meanings.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

Where ranges are provided, it is to be understood that the range refers not just to the specified range, but that it also encompasses any sub-range of or any single value within the recited range, even if not specifically recited.

The definition of each expression, e.g., alkyl, or the like, when it occurs more than once in any structure, is intended to be independent of its definition elsewhere in the same structure.

An "ubiquitin ligase binder" of the present invention is a moiety (e.g., a small molecule) that binds to an ubiquitin ligase. In certain embodiments, the ubiquitin ligase is an E3 ubiquitin ligase.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" (i.e., the attachment is via the last portion of the name) unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, and —$CH_2CH(CH_2CH_3)CH_2$—.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thioxo groups.

Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thioxo.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thioxo. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thioxo.

The term "halo" or "halogen" as used herein, means —Cl, —Br, —I or —F.

The terms "haloalkyl" and "haloalkoxy" refer to an alkyl or alkoxy group, as the case may be, which is substituted with one or more halogen atoms.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thioxo. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, 2,3-dihydrothieno[3,4-b][1,4]dioxan-5-yl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thioxo.

The terms "heterocyclyl" as used herein, mean a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thioxo. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thioxo.

The term "oxo" as used herein means a =O group.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Subject" refers to a warm-blooded animal such as a mammal, preferably a human, or a human child, which is afflicted with, or has the potential to be afflicted with one or more diseases and disorders described herein.

As used herein, the terms "treat," "treating," and "treatment" mean implementation of therapy with the intention of reducing in severity or frequency symptoms, elimination of symptoms or underlying cause, prevention of the occurrence of symptoms or their underlying cause, or the improvement or remediation of damage due to a disease, disorder, or condition.

The terms as defined above are also intended to include variations of the terms as would be used and understood by one of skill in the art. In a non-limiting example, "substituted" as defined herein refers not only to "substituted," but also to "substitution," "substituted with," and the like.

Compounds

In a first aspect, the disclosure provides a compound of Formula I:

$$P\text{-}L\text{-}U \qquad (I)$$

or a pharmaceutically acceptable salt thereof, wherein
P is a FOXO1 fusion protein binding moiety;
L is a bivalent linker; and
U is an ubiquitin ligase binding moiety.

In one embodiment of the first aspect of the invention, the disclosure provides a compound wherein P is of Formula II:

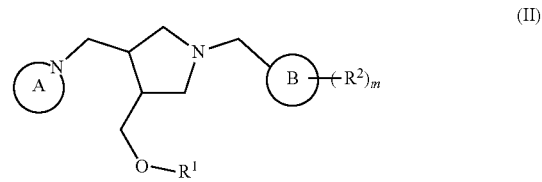

wherein
m is an integer 0, 1, or 2;
ring A represents a 6- or 7-member heterocyclyl optionally substituted with one or two $R^3$;
ring B represents an aryl, heteroaryl, heterocyclyl, or $C_4$-$C_8$ cycloalkyl;
$R^1$ is hydrogen, $C_1$-$C_6$ alkyl, $C_1$-$C_6$ haloalkyl, or a bond to L; and
each $R^2$ is independently halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, aryl optionally substituted with one or more $R^4$, heteroaryl optionally substituted with one or more $R^4$, heterocyclyl optionally substituted with one or two $R^5$, or $C_4$-$C_8$ cycloalkyl optionally substituted with one or more $R^5$, or $R^2$ is a bond to L provided that only one bond to L is present in P; where
each $R^3$ is independently selected from halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy, or $R^3$ groups when attached to the same carbon atom form =O;

each $R^4$ is independently selected from halogen, $-NO_2$, $-CN$, $C_1$-$C_6$ alkyl, $C_1$-$C_6$ haloalkyl, $-NH_2$, $-NH(C_1$-$C_6$ alkyl), $-N(C_1$-$C_6$ alkyl)$_2$, $-OH$, $C_1$-$C_6$ alkoxy, and $C_1$-$C_6$ haloalkoxy;

each $R^5$ is independently selected from halogen, $-NO_2$, $-CN$, $C_1$-$C_6$ alkyl, $C_1$-$C_6$ haloalkyl, $-NH_2$, $-NH(C_1$-$C_6$ alkyl), $-N(C_1$-$C_6$ alkyl)$_2$, $-OH$, $C_1$-$C_6$ alkoxy, and $C_1$-$C_6$ haloalkoxy, or $R^5$ groups when attached to the same carbon atom form $=O$.

In certain embodiments, ring A of Formula II is azepanyl, 1,4-diazepanyl, 1,4-oxazepanyl, morpholinyl, piperazinyl, or piperidinyl, each optionally substituted with one or two $R^3$.

In other embodiments, ring A of Formula II is azepanyl, 1,4-diazepanyl, or morpholinyl, each optionally substituted with one or two $R^3$.

In certain embodiments, each $R^3$ is independently $C_1$-$C_4$ alkyl or $C_1$-$C_4$ haloalkyl.

In certain embodiments, ring A of Formula II is 4-methyl-1,4-diazepan-1-yl, such that P is of formula (III):

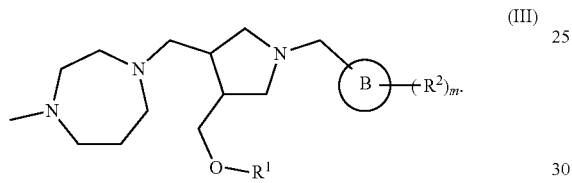

(III)

In certain embodiments, ring B of Formula II is an aryl or heteroaryl.

In certain embodiments, ring B of Formula II is phenyl.

In certain embodiments, ring B of Formula II is a 5-member heteroaryl.

In certain embodiments, ring B of Formula II is pyrazole or imidazole.

In certain embodiments, ring B of Formula II is pyrazol-4-yl, such that P is of formula (IV):

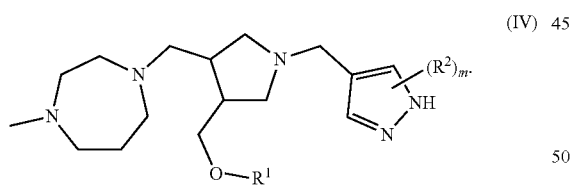

(IV)

In certain embodiments, m is 1 or 2.

In certain embodiments, at least one $R^2$ is aryl optionally substituted with one or more $R^4$, heteroaryl optionally substituted with one or more $R^4$, heterocyclyl optionally substituted with one or two $R^5$, or $C_4$-$C_8$ cycloalkyl optionally substituted with one or more $R^5$.

In certain embodiments, at least one $R^2$ is phenyl optionally substituted with one or more $R^4$.

In certain embodiments, at least one $R^2$ is a bond to L.

In certain embodiments, $R^1$ is hydrogen, $C_1$-$C_4$ alkyl, or $C_1$-$C_4$ haloalkyl; or $R^1$ is hydrogen, $C_1$-$C_2$ alkyl, or $C_1$-$C_2$ haloalkyl; or $R^1$ is hydrogen or methyl; or $R^1$ is hydrogen.

In certain embodiments, $R^1$ is a bond to L.

In certain embodiments, P of Formula II is:

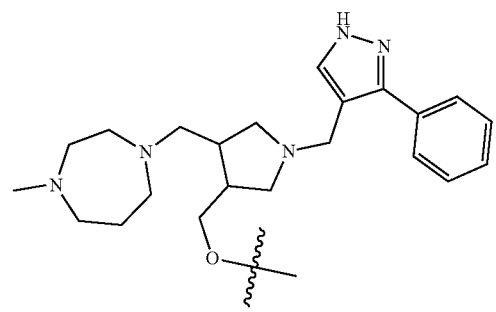

,

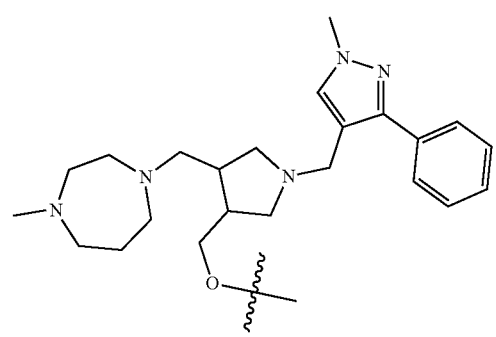

,

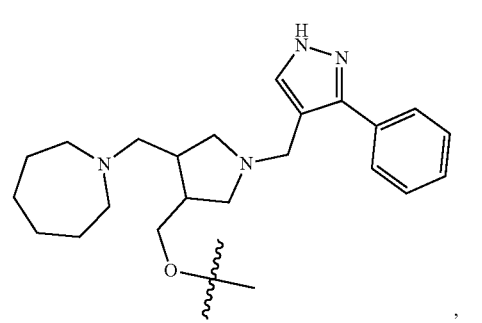

,

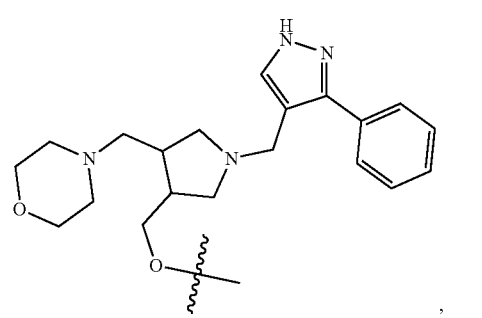

,

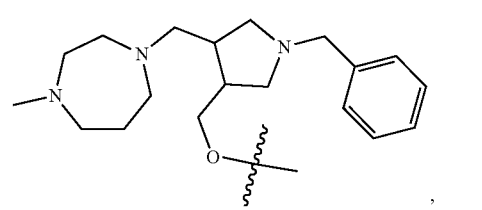

,

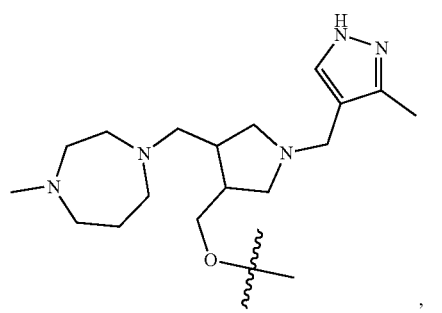
,
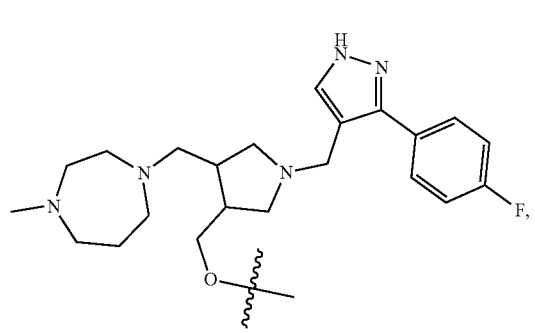
,
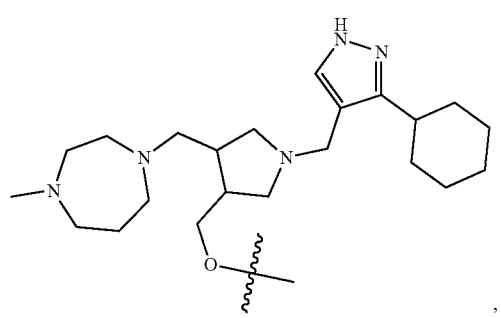
,
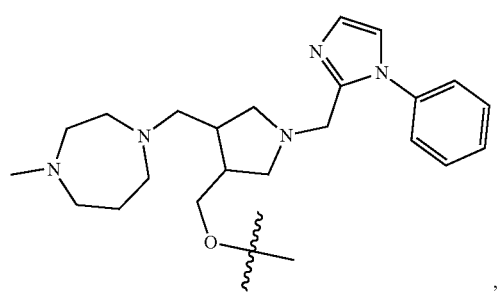
,
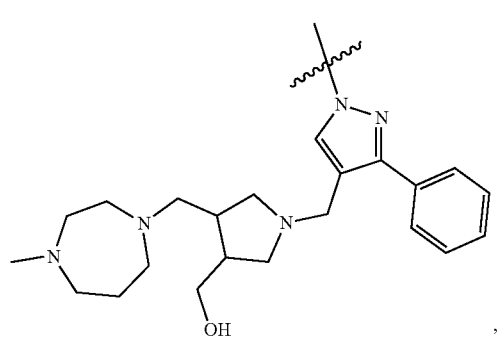
,
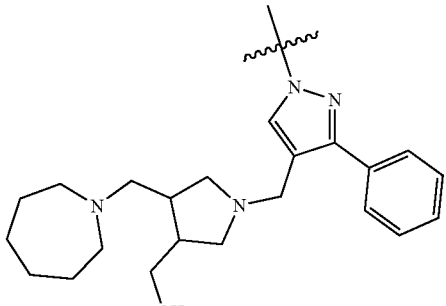
,
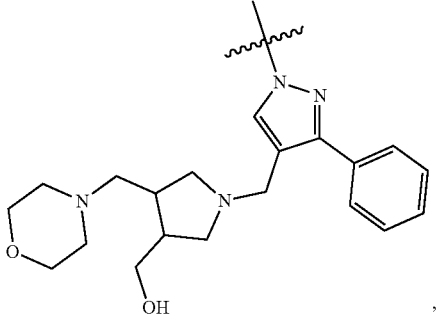
,
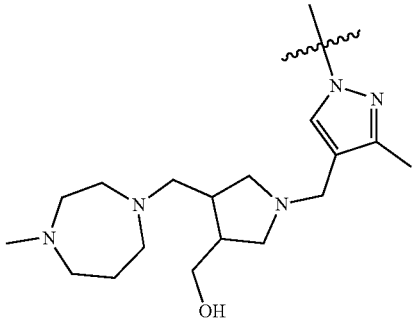
,
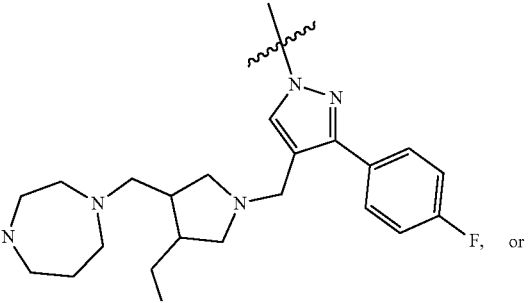 or
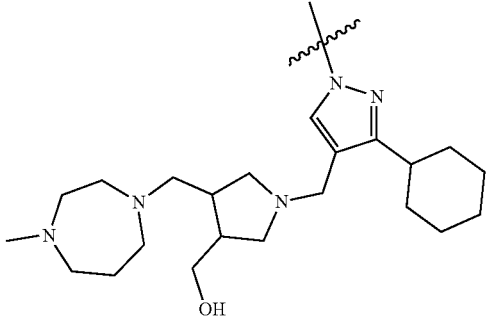

In certain embodiments, P is

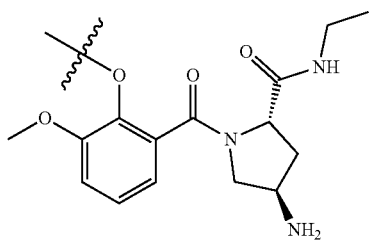 or

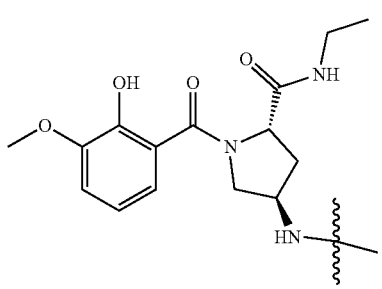

In certain embodiments, P is a PAX3-FOXO1 fusion protein binding moiety. In certain embodiments P is a PAX7-FOXO1 fusion protein binding moiety.

In certain embodiments, L is

In certain embodiments, U is Cereblon (CRBN) E3 ligase moiety:

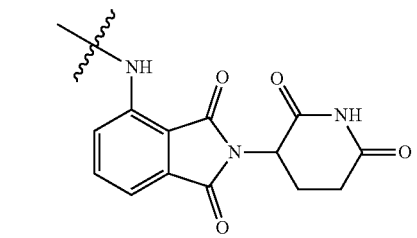 [SMILES: *Nc1cccc2c1C(=O)N(C1CCC(=O)NC1=O)C2=O]

((2-(2,6-dioxopiperidin-3-yl)-1,3-dioxoisoindolin-4-yl) amino).

In certain embodiments, U is Von Hippel Lindau (VHL) E3 ubiquitin ligase moiety:

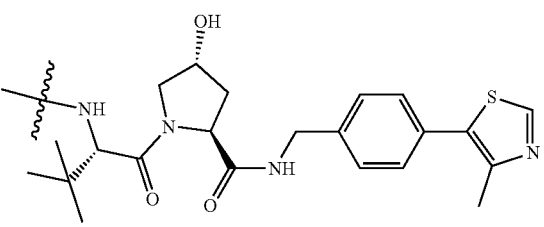 [SMILES: *N[C@H](C(=O)N1C[C@H](O)C[C@H]1C(=O)NCc1ccc(-c2scnc2C)cc1)C(C)(C)C]

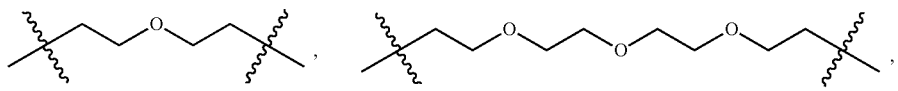

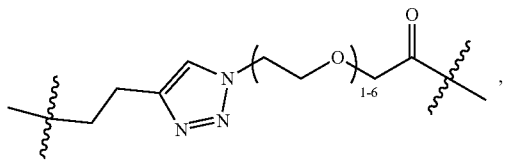,

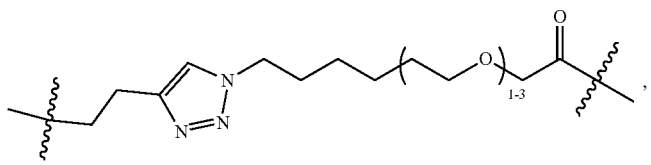,

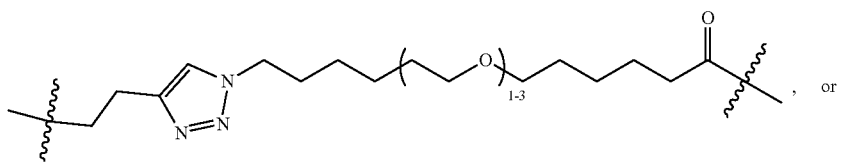, or

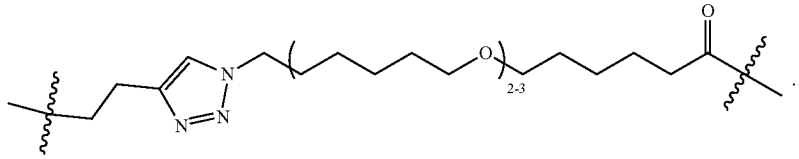.

(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino).

In certain embodiments, the E3 ligase binder may be modified for better selectivity and stability.

In certain embodiments, the compounds useful as FOXO1 fusion protein binding moieties include, but are not limited, to:

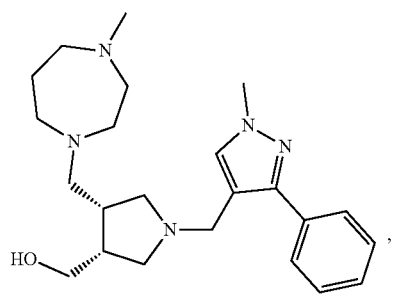
,

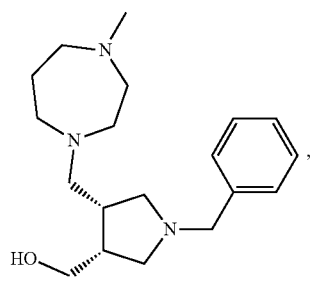
,

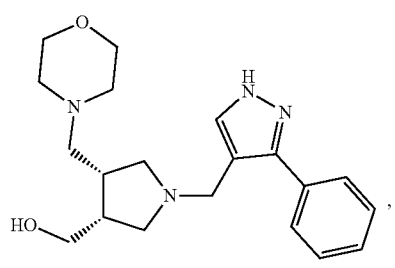
,

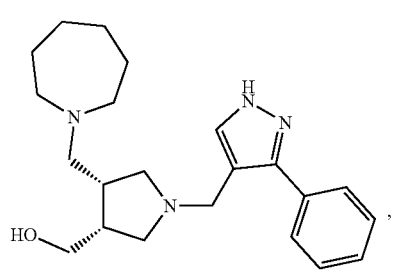
,

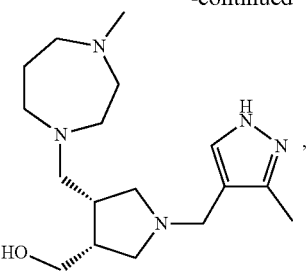
,

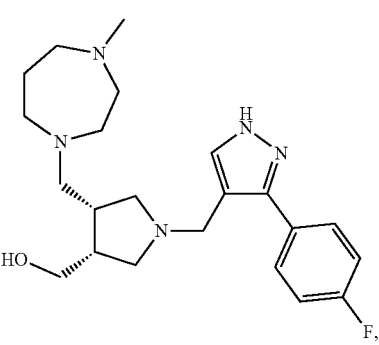
,

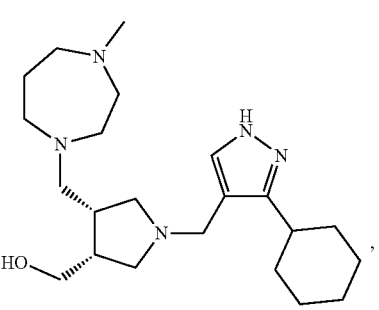
, and

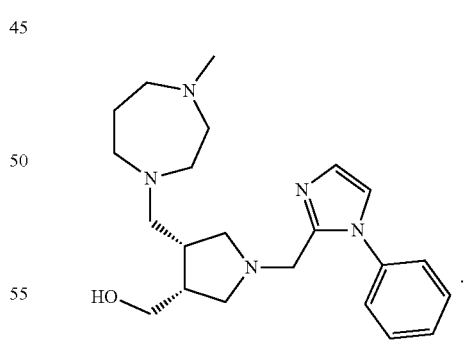
.

Figure 1B:
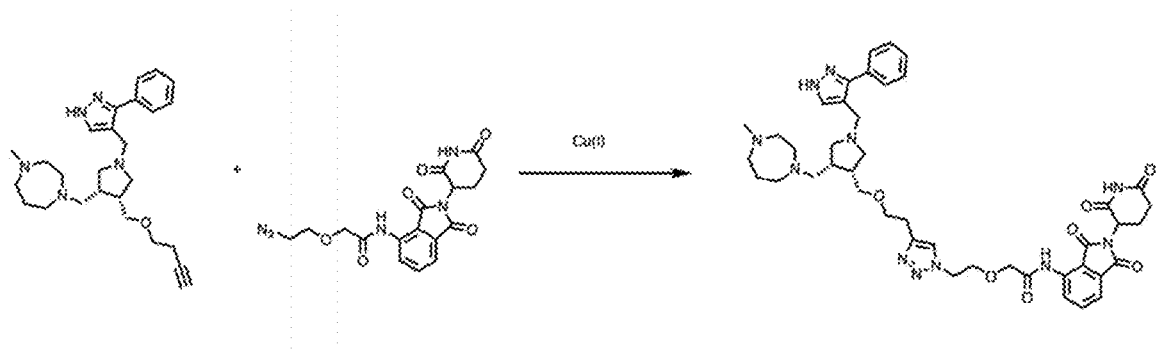

Synthesis of the compounds of the disclosure is within the purview of one of skill in the art. In particular, in certain embodiments, the compounds of the disclosure may be prepared by a modular "Click" chemistry-based approach (see, FIG. 1).

In certain embodiments, following azides may be used to perform a "Click" reaction with alkynyl-functionalized P to arrive at the compounds of formula (I):

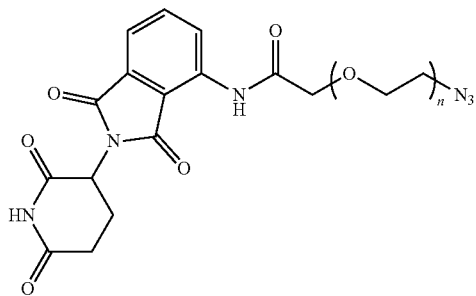

n = 1-6

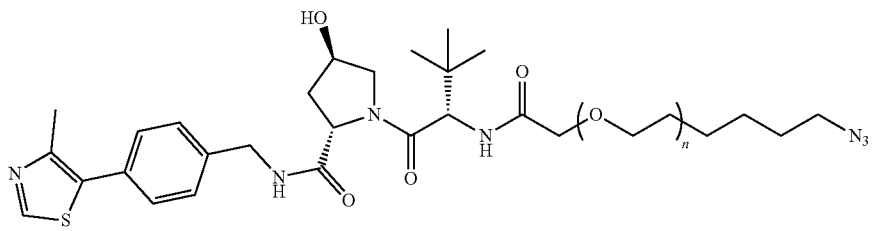

n = 2

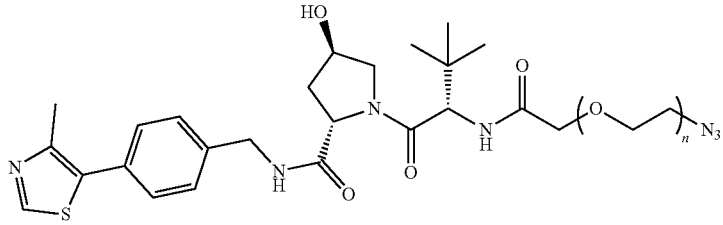

n = 1, 3, 4

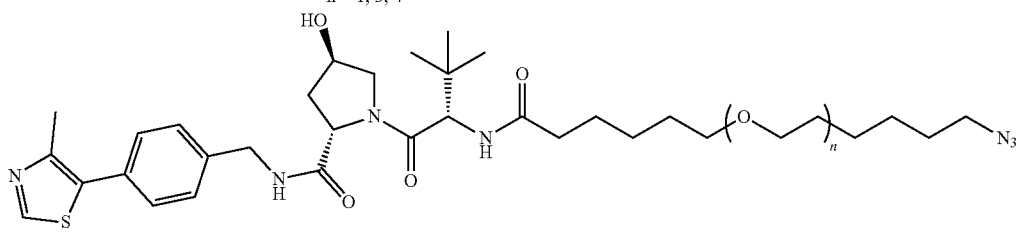

n = 3

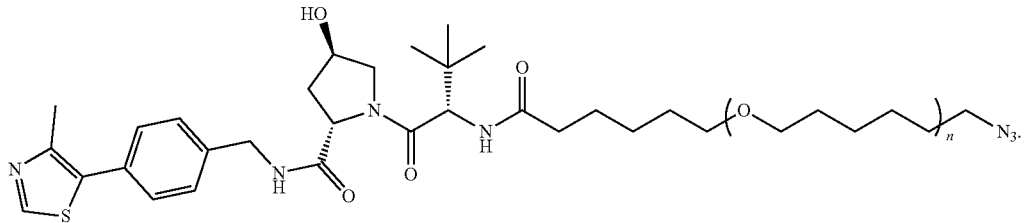

n = 2

The present invention encompasses all suitable combinations of the various embodiments of each aspect of the invention as disclosed above. Thus, it is to be understood that all combinations of embodiments resulting in a stable compound are to be regarded as disclosed herein, even if not specifically recited. Combinations of substituents and/or variables are permissible only if such combinations result in stable compounds. A stable compound or stable structure is meant to imply a compound that is sufficiently robust to survive isolation from a reaction mixture, and subsequent formulation into an effective therapeutic agent. It is within the purview of one of skill in the art to envision various sub-genera and stable compounds based on the disclosure herein, and accordingly each possible sub-genus and compound is to be considered specifically disclosed herein.

Certain compounds are described herein using a general formula that includes variables, e.g. $R^1$ and $R^2$. Unless otherwise specified, each variable within such a formula is defined independently of other variables. Thus, if a group is said to be substituted, e.g. with 0-2 R*, then said group may be substituted with up to two R* groups and R* at each occurrence is selected independently from the definition of R*.

When ranges are specified with respect to particular moieties, it is to be understood that all options and subranges within the range are included, even if not specifically enumerated. For example, $C_1$-$C_6$ alkyl includes $C_1$ alkyl, $C_2$ alkyl, $C_3$ alkyl, $C_4$ alkyl, $C_6$ alkyl, and $C_6$ alkyl, as well as $C_2$-$C_6$ alkyl, $C_2$-$C_4$ alkyl, etc.

The compounds of the present disclosure may have asymmetric centers. Compounds of the present disclosure containing an asymmetrically substituted atom may be isolated in optically active or racemic forms. It is known in the art how to prepare optically active forms, such as by resolution of materials. All chiral, diastereomeric, all mixtures of chiral or diastereomeric forms, and racemic forms are within the scope of this disclosure, unless the specific stereochemistry or isomeric form is specifically indicated. It will also be understood by a person of ordinary skill in the art that when a compound is denoted as (R) or (S) stereoisomer, it may contain the corresponding (S) or (R) stereoisomer as an impurity preferably the undesired enantiomer is present in less than about 10%, preferably 5% w/w. About means + or −10% of initial value.

Certain compounds of the present disclosure can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group even if not specifically recited herein. Similarly, when the cyclic groups such as aryl, heteroaryl, heterocyclyl are substituted, they include all the positional isomers even if not specifically recited herein. Furthermore, all hydrates of a compound of the present disclosure are within the scope of this disclosure.

The present disclosure also includes protected derivatives of compounds of the disclosure. For example, when compounds of the present disclosure contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of the present disclosure can be prepared by methods well known in the art.

Pharmaceutical Compositions and Administration

Compounds disclosed herein can be administered as the neat chemical, but are preferably administered as a pharmaceutical composition. Accordingly, in a second aspect, the present disclosure provides compositions comprising the compounds of the invention and a pharmaceutically acceptable carrier, excipient, or diluent. Use of the phrase "pharmaceutically acceptable carrier, excipient, or diluent" is intended to encompass a single or a mixture of pharmaceutically acceptable ingredients.

Acceptable carriers, excipients, and diluents are nontoxic, aid administration, and do not adversely affect the therapeutic benefit of the compound of this disclosure. They must be of sufficiently high purity and sufficiently low toxicity to render them suitable for administration to the subject being treated. They may be inert or they may possess pharmaceutical benefits of their own. They may be any solid, liquid, semi-solid or, in the case of an aerosol composition, gaseous excipient. The amount of carrier, excipient or diluent employed in conjunction with the compound is sufficient to provide a practical quantity of material for administration per unit dose of the compound.

Suitable carriers, excipients, and diluents are known to those of skill in the art. They may include, but are not limited to, solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like; and liquid and semisolid excipients such as glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

Optional active agents may be included in a pharmaceutical composition, which do not substantially interfere with the activity of the compound of the present invention.

The compounds of this disclosure may be used in combination with one or more other drugs in the treatment of diseases or conditions for which compounds of this disclosure or the other drugs may have utility. Such other drug(s) may be administered by a route and in an amount commonly used therefor, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

Compounds disclosed herein may be administered orally, topically, parenterally, by inhalation or spray, sublingually, transdermally, via buccal administration, or by other means routine in the art for administering pharmaceutical compositions. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

In general, the compounds of this disclosure will be administered in a therapeutically effective amount by any of the accepted modes of administration for agents that serve similar utilities. Therapeutically effective amounts of compounds of this disclosure may range from about 0.01 to about 500 mg per kg patient body weight per day, which can be administered in single or multiple doses. A suitable dosage level may be from about 0.1 to about 250 mg/kg per day; or about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the patient, the potency of the compound being utilized, the route and form of administration, and other factors.

Methods

The compounds as disclosed herein are useful as binders of PAX3-FOXO1. Accordingly, in a third aspect, the disclosure provides a method of treating cancer, wherein the method comprises administering to a subject in need of such treatment a compound or a pharmaceutical composition of the disclosure.

In certain embodiments, the cancer is rhabdomyosarcoma, and in certain embodiments, the rhabdomyosarcoma is fusion positive rhabdomyosarcoma (FP-RMS).

In other embodiments, the cancer may be, but is not limited to, breast cancer, prostate cancer, colon carcinoma, ovarian cancer, multiple myeloma, B-chronic lymphocytic leukemia, chronic myelogenous leukemia, or non-Hodgkin lymphoma.

In certain embodiments, the cancer is non-Hodgkin lymphoma, and in certain embodiments, the non-Hodgkin lymphoma is diffuse large B-cell lymphoma (DLBCL).

In a fourth aspect, the disclosure provides a compound or a pharmaceutical composition of the disclosure for treating cancer. In certain embodiments of this aspect of the disclosure, the cancer is rhabdomyosarcoma. In certain embodiments, the rhabdomyosarcoma is FP-RMS.

Both human and non-human subjects are within the scope of the disclosure. Non-human subjects include, but are not limited to, fish, amphibians, reptiles or birds, but a particular embodiment of the disclosure includes treating mammals, including non-human mammals such as rodents (rats, guinea pigs), companion animals (e.g. cats, dogs), or livestock animals (sheep, goats, pigs, cattle, horses). In certain embodiments, the subject is a mammal, and in other embodiments, the subject is a human.

In a fifth aspect, the present disclosure provides a method of ubiquitinating a PAX3-FOXO1 fusion protein in a cell, the method comprising administering a compound or a pharmaceutical composition of the disclosure to the cell. Administration may be in vitro, ex vivo, or in vivo.

The following examples are provided to enable those skilled in the art to more clearly understand and practice the present disclosure. They should not be considered as limiting the scope of the disclosure, but merely as being illustrative and representative thereof.

EXAMPLES

Example 1: Screening for Target Binders

Figure 2A:
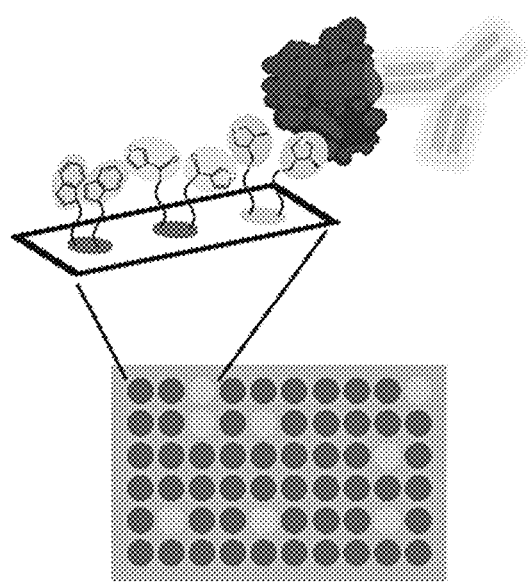
FIG. 2A and FIG. 2B depict the molecule microarray (SMM) screens used to identify binders of PAX3-FOXO1.
Figure 2B:
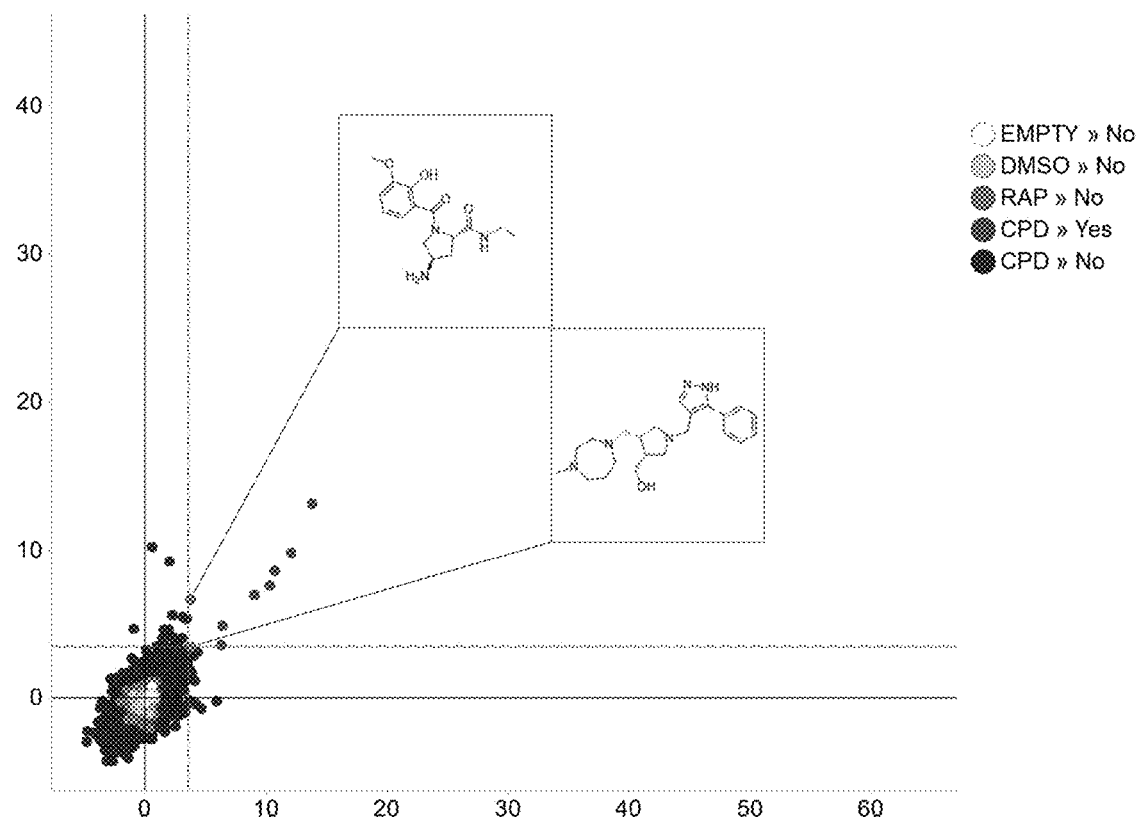

The PAX3-FOXO1 fusion protein was transiently overexpressed with a FLAG epitope tag in HEK293T cells to enable a small molecule microarray (SMM) screen against 10,000 molecules in a pilot screen. (FIG. 2A). Identification of putative hits in the SMM screens was determined by signal-to-noise ratio analysis for the fluorescence signal of each printed feature. The average performance of each compound in two technical replicate screens (FIG. 2B) were plotted together with the performance data for several control populations (e.g. microarray features printed from "DMSO" or "empty" wells and "rapamycin," an unrelated molecule). With a z score threshold of 3.5, ten compounds were identified as assay positives. After filtering out compounds that scored in a counter screen of untransfected lysates or were found to score well in multiple screens of other unrelated targets (i.e. nonspecific positives), we identified two selective compounds that were promoted into follow-up assays.

Example 2: CETSA Assays

Figure 3A:
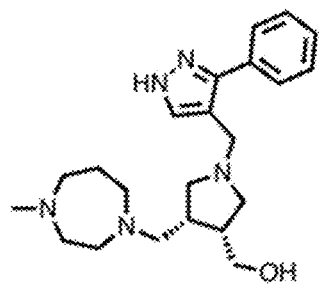
FIG. 3A, FIG. 3B, and FIG. 3C show that KI-P3F-032 is a functionally "silent" direct binder of PAX3-FOXO1 and FOXO1.
Figure 3B:
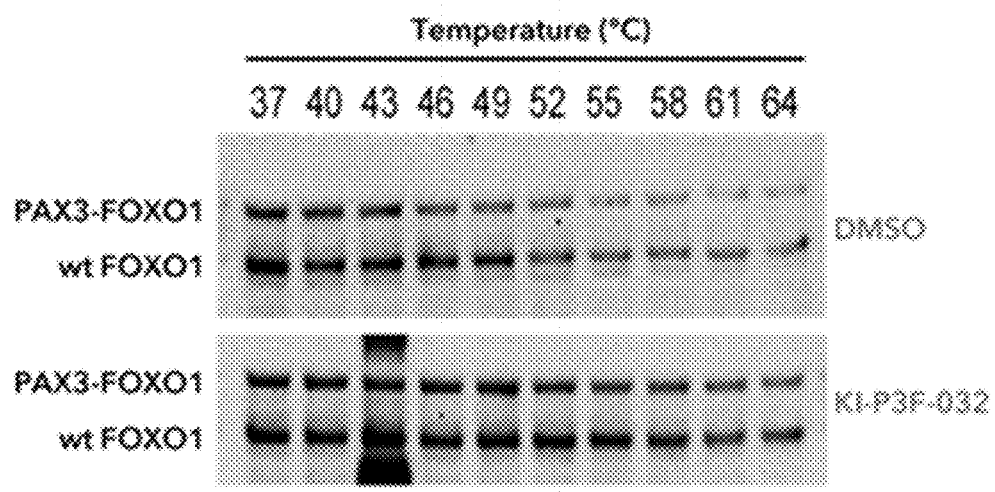
Figure 3C:
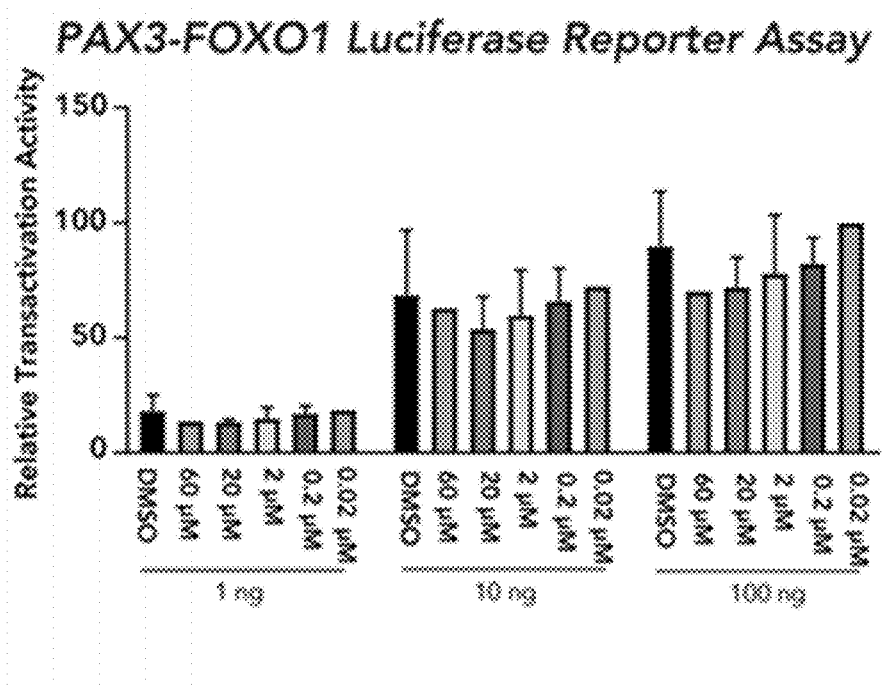

We performed cellular thermal shift assays (CETSA) to measure binding to PAX3-FOXO1 using lysates from FP-RMS cells. One of the two compounds, KI-P3F-032 (FIG. 3A), significantly increased the melting temperature of PAX3-FOXO1 at a dose of 20 µM (FIG. 3B). The compound also stabilizes wild type FOXO1, a target of interest for gastric cancer, lymphomas, and Type 2 diabetes, suggesting that the compound binds to this portion of the fusion protein; preliminary experiments suggest wild type PAX3 is not stabilized. Next, we performed luciferase reporter assays with KI-P3F-032 based on the PAX3-FOXO1-dependent ALK enhancer, finding that this molecule does not significantly affect PAX3-FOXO1 function (FIG. 3C). Thus, we decided to pursue KI-P3F-032 as a ligand for PAX3-FOXO1 proteolysis targeting chimaeras (PROTACs) to utilize this ligand for therapeutic benefit.

Example 3: PAL Experiments

We validated the direct binding of KI-P3F-032 to PAX3-FOXO1 using photoaffinity labeling (PAL) experiments, a gold standard for cellular target engagement. In these experiments, we synthesized derivatives ("photoprobes") of KI-P3F-032 that contained a photoactivatable diazirine moiety, along with an alkyne moiety for use as a "Click" chemistry handle. Upon irradiation with 365 nm light, the diazirine loses molecular nitrogen and forms a reactive carbene that crosslinks with any biomolecules to which the photoprobe is bound. After photoirradiation, either a fluorophore (for in-gel fluorescence) or biotin (for affinity enrichment and streptavidin-based detection) is attached to the crosslinked molecule-target complexes via the alkyne moiety.

Figure 4A:
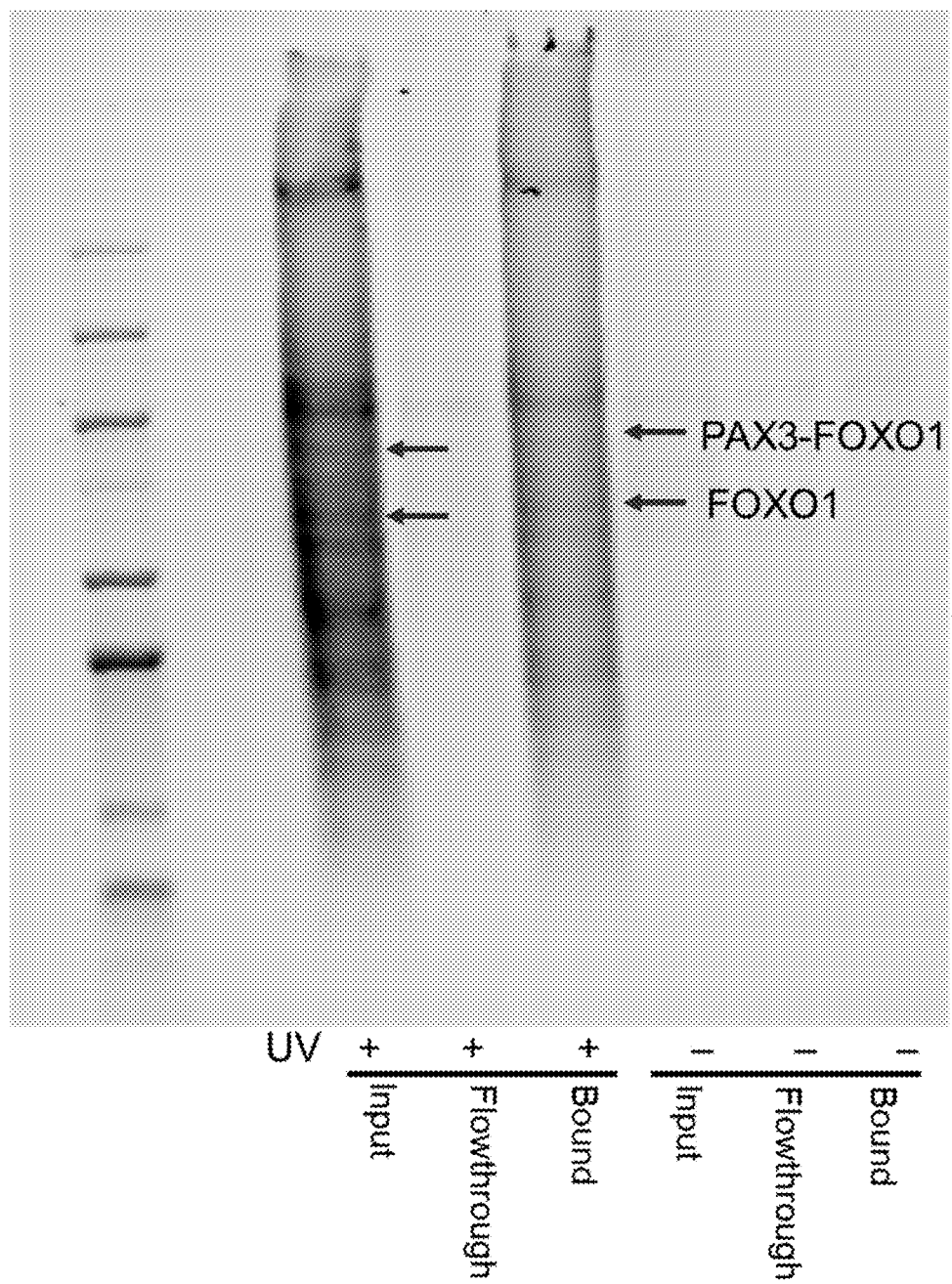
FIG. 4A, FIG. 4B, and FIG. 4C show photoaffinity labeling (PAL) experiments and confirms that PAX3-FOXO1 and FOXO1 are direct targets of KI-P3F-032.
Figure 4B:
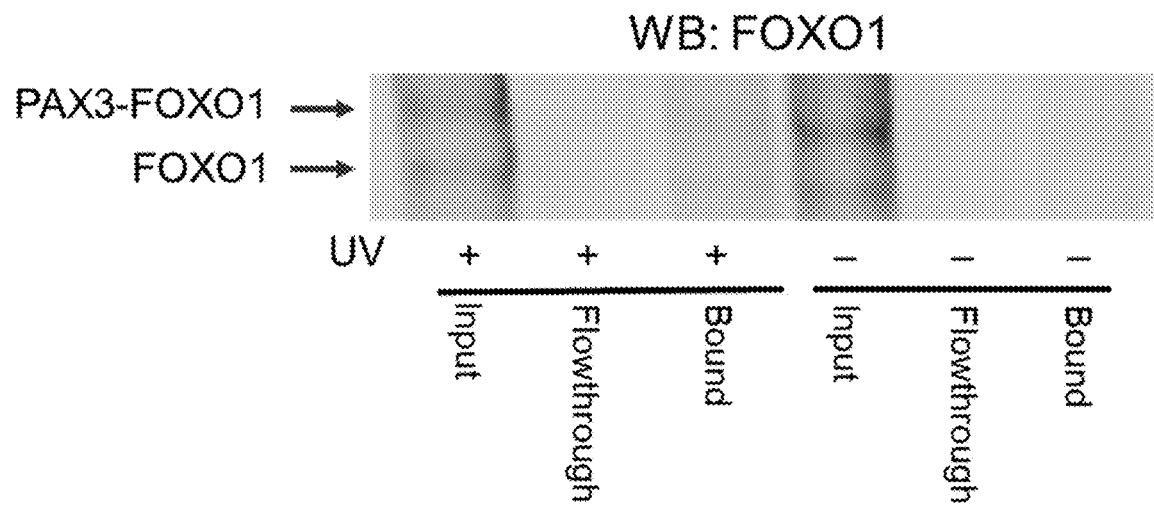
Figure 4C:
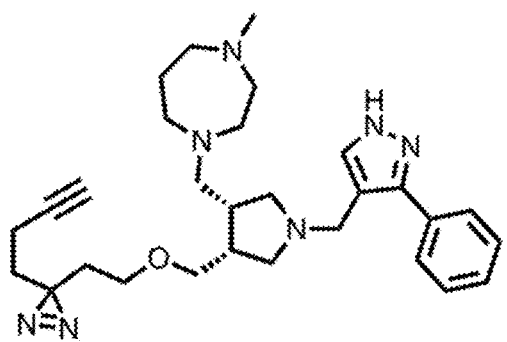

Indicating that PAX3-FOXO1 is a direct target of KI-P3F-032, we observed photoprobe bands with identical molecular weights to both PAX3-FOXO1 and FOXO1 in gel-based PAL experiments (FIG. 4). To confirm these bands are indeed PAX3-FOXO1 and FOXO1, we performed PAL experiments with biotin conjugation followed by affinity enrichment and detected PAX3-FOXO1 and FOXO1 via a western blot. Strikingly, we observed enrichment of PAX3-FOXO1 and FOXO1 only when the sample was treated with UV light (untreated samples are unable to undergo the crosslinking reaction).

Example 4: Dose Response Experiments

Figure 5:
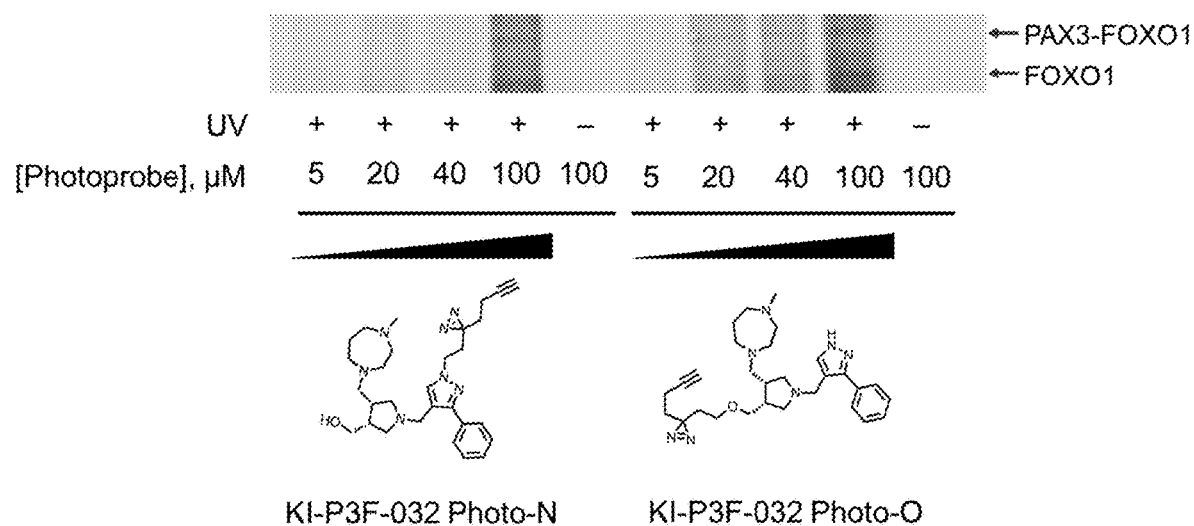
FIG. 5 shows the results of dose response Photo-KI-P3F-032 experiments using N- and O— linked photoprobes.

Dose response of Photo-KI-P3F-032 experiments were performed using Rh4 nuclear lysates and A647 conjugation (FIG. 5). We observed that the O-linked photoprobe appeared to bind more tightly than the N-linked probe.

Example 5: Binding to Targets in Nuclear vs. Cytosolic Lysates

Figure 6:
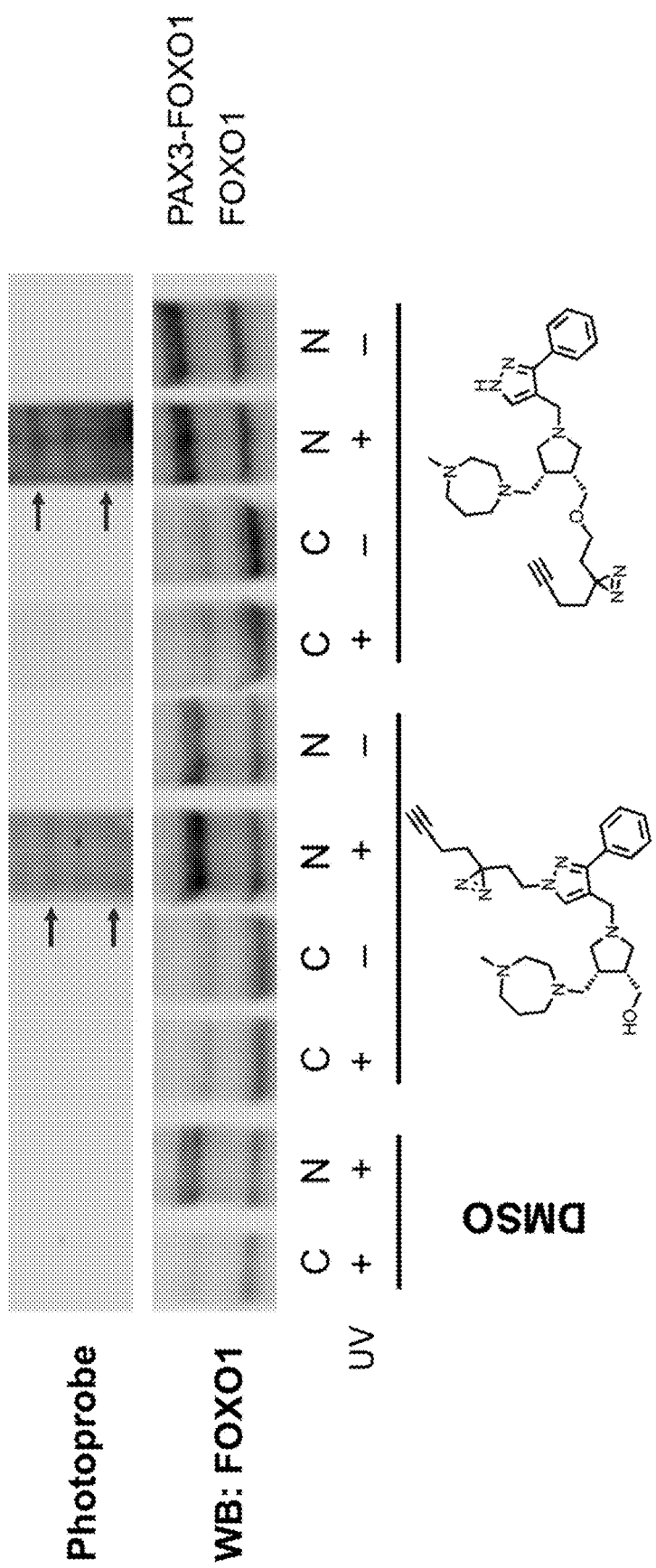
FIG. 6 shows results of photoaffinity experiments performed with both Rh4 nuclear and cytosolic lysates.

Photoaffinity experiments with Photo-KI-P3F-032 were performed with both Rh4 nuclear and cytosolic lysates (FIG. 6). We observed that labeling only occurs in the nuclear fraction, even though a significant portion of FOXO1 is present in the cytosol.

Example 6: Competitive In-Cell Photoaffinity Labeling

Figure 7:
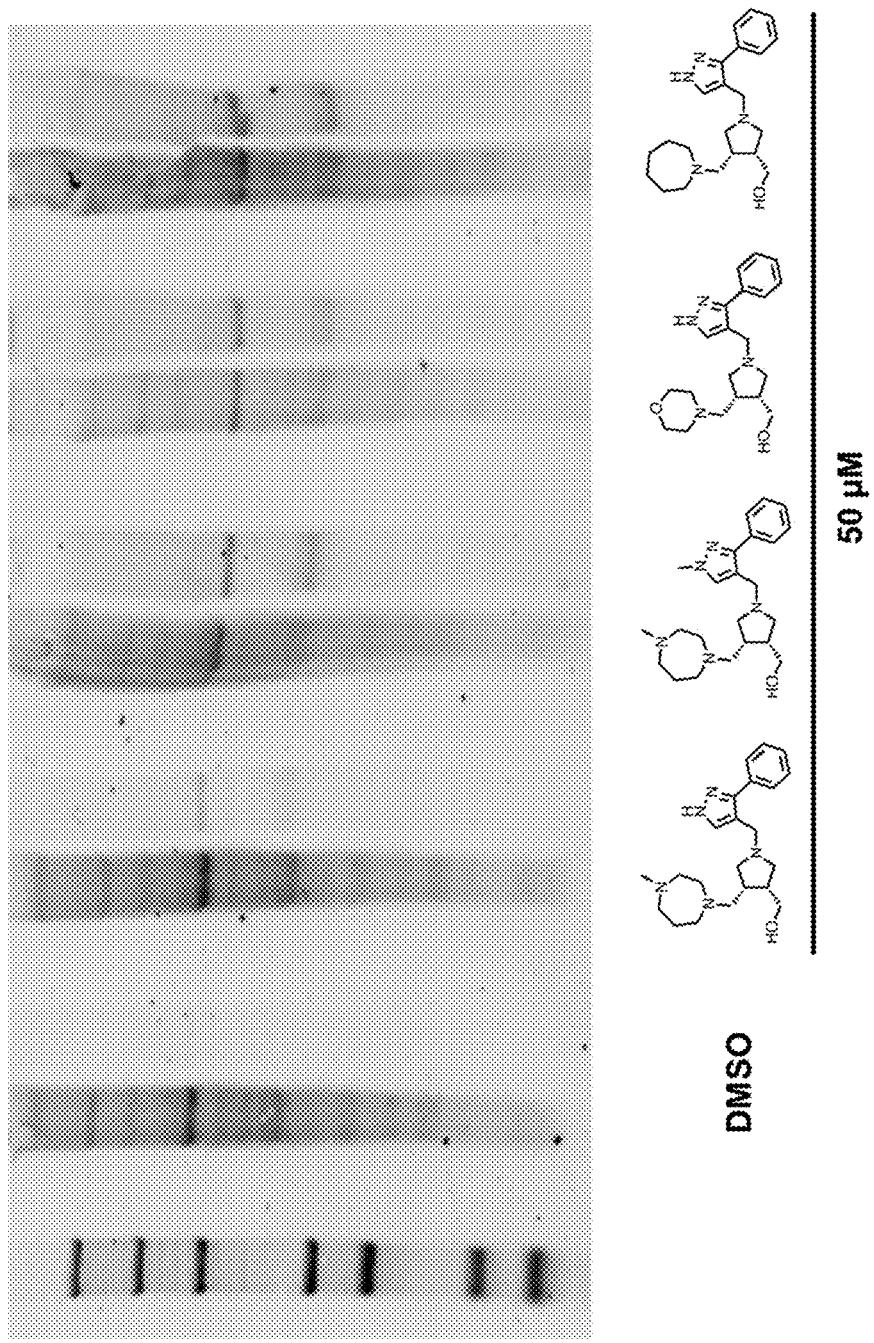
FIG. 7 shows results of in-cell photoaffinity competition experiments.

In-cell photoaffinity competition experiments were performed with KI-P3F-032 analogues and KI-P3F-032 Photo-O (FIG. 7). Reduced crosslinking when a competitor is present indicates binding of the analogue to the same site as KI-P3F-032 Photo-O. We observed that some analogues appeared to bind more strongly (i.e., compete better) than the parent molecule.

Example 7: Photoaffinity Experiments with P3F KD Line

Figure 8:
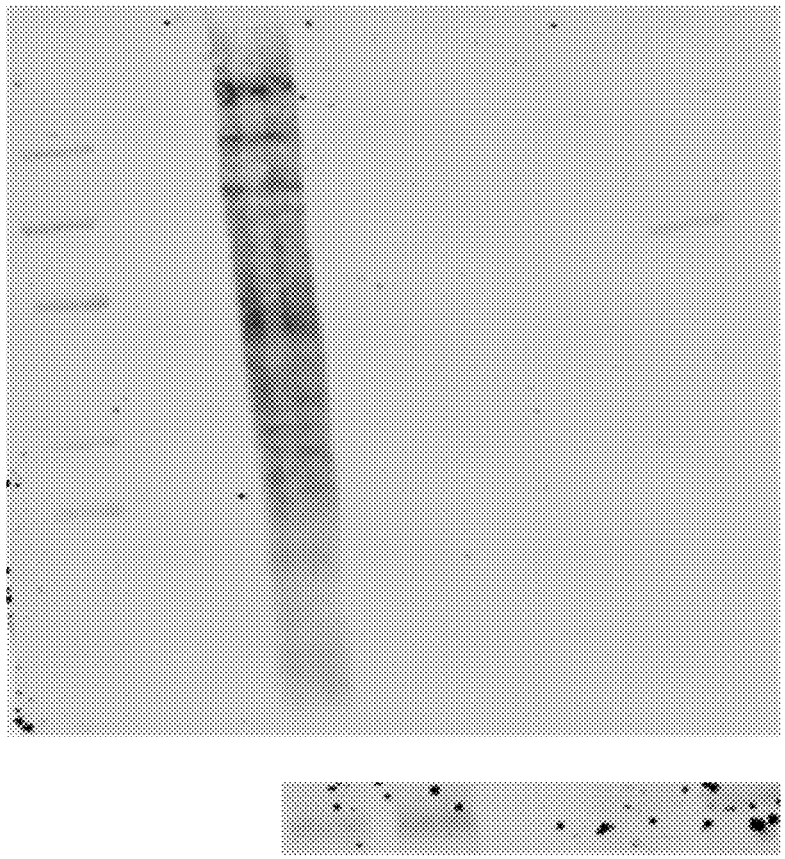
FIG. 8 shows results of in-cell photoaffinity experiments were performed with an Rh4 line with a doxycycline inducible breakpoint targeted PAX3-FOXO1 shRNA.

In-cell photoaffinity experiments were performed with an Rh4 line with a doxycycline inducible breakpoint targeted PAX3-FOXO1 shRNA (FIG. 8). We observed that knockdown of PAX3-FOXO1 in Rh4 cells completely eliminated all photoaffinity labeling by KI-P3F-032 Photo-0.

REFERENCES

1. Gryder, B. E. et al. PAX3-FOXO1 Establishes Myogenic Super Enhancers and Confers BET Bromodomain Vulnerability. *Cancer Discov* 7, 884-899 (2017).
2. Gryder, B. E. et al. Miswired Enhancer Logic Drives a Cancer of the Muscle Lineage. *iScience* 23, 101103 (2020).
3. Henley, M. J. & Koehler, A. N. Advances in targeting 'undruggable' transcription factors with small molecules. *Nat Rev Drug Discov* 20, 669-688 (2021).
4. Wachtel, M. & Schäfer, B. W. PAX3-FOXO1: Zooming in on an "undruggable" target. *Seminars in Cancer Biology* 50, 115-123 (2018).
5. Sakamoto, K. M. et al. Protacs: Chimeric molecules that target proteins to the Skp1-Cullin-F box complex for ubiquitination and degradation. *Proceedings of the National Academy of Sciences* 98, 8554-8559 (2001).
6. Nalawansha, D. A. & Crews, C. M. PROTACs: An Emerging Therapeutic Modality in Precision Medicine. *Cell Chemical Biology* 27, 998-1014 (2020).
7. Leifer, B. S. et al. An Array-Based Ligand Discovery Platform for Proteins With Short Half-Lives. in *Methods in Enzymology* vol. 610 191-218 (Elsevier, 2018).
8. Molina, D. M. et al. Monitoring Drug Target Engagement in Cells and Tissues Using the Cellular Thermal Shift Assay. *Science* 341, 84-87 (2013).
9. Flaxman, H. A. & Woo, C. M. Mapping the Small Molecule Interactome by Mass Spectrometry. *Biochemistry* 57, 186-193 (2018).
10. Wurz, R. P. et al. A "Click Chemistry Platform" for the Rapid Synthesis of Bispecific Molecules for Inducing Protein Degradation. *J. Med. Chem.* 61, 453-461 (2018).
11. Rankovic, Z. et al. Phenyl-Glutarimides: Alternative Cereblon Binders for the Design of PROTACs. *Angew. Chem. Int. Ed.* anie. 202108848 (2021) doi:10.1002/anie.202108848.
12. Siriwardena, S. U. et al. Phosphorylation-Inducing Chimeric Small Molecules. *J. Am. Chem. Soc.* 142, 14052-14057 (2020).

What is claimed is:

1. A compound of formula (I):

P—L—U (I)

or a pharmaceutically acceptable salt thereof, wherein P is a FOXO1 fusion protein binding moiety and is:

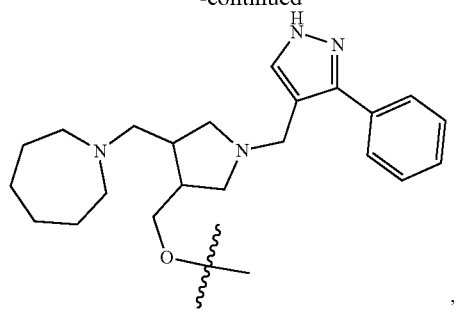,
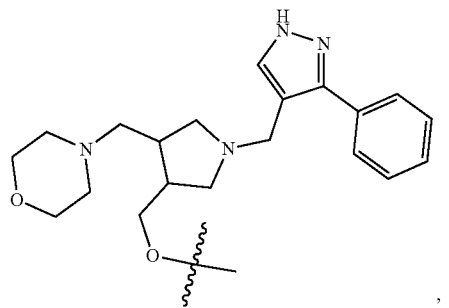,
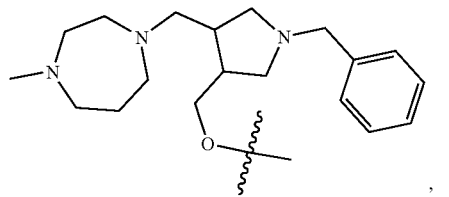,
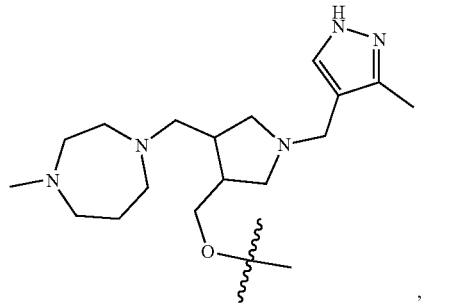,
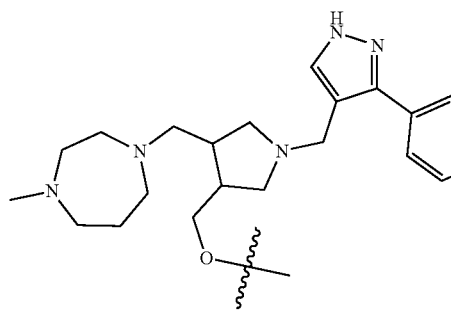,
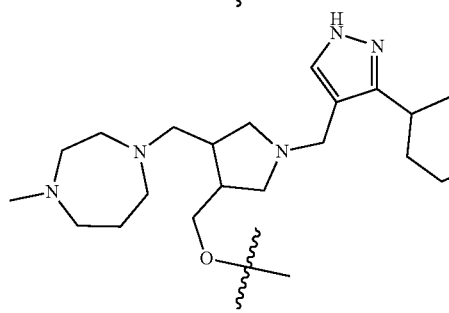,
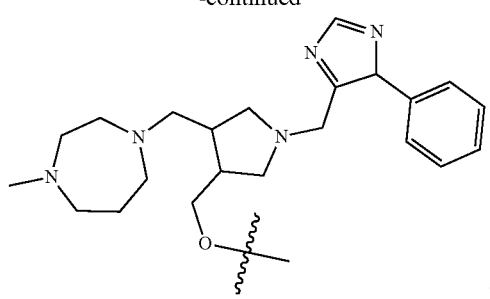,
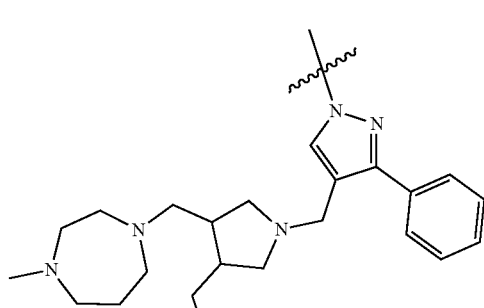,
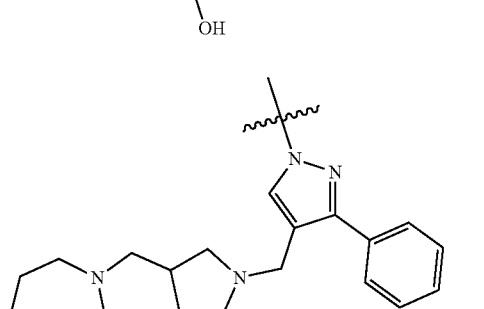,
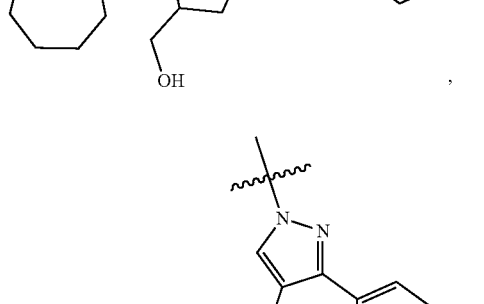,
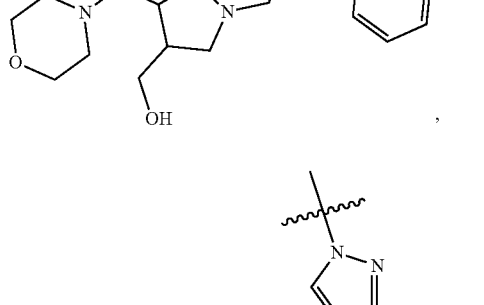,
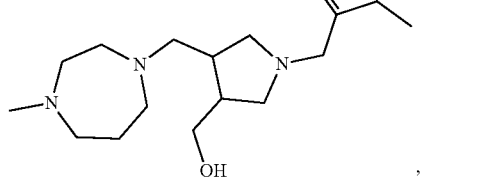, -continued

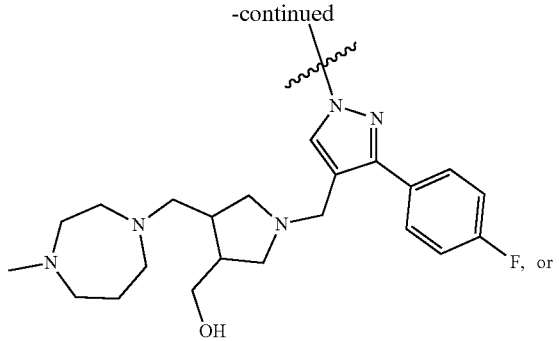

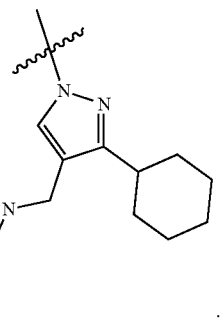

L is a bivalent linker and is

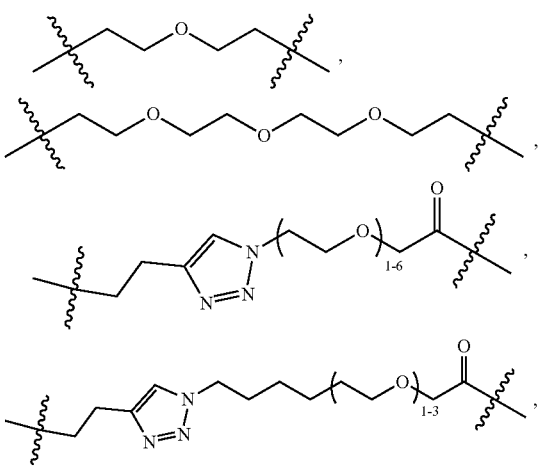

-continued

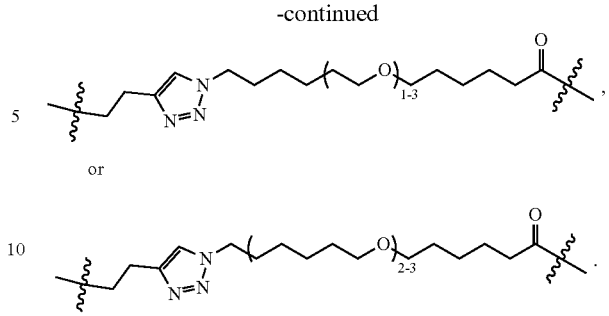

or

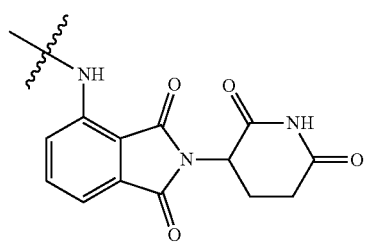 [SMILES: *Nc1cccc2c1C(=O)N(C1CCC(=O)NC1=O)C2=O]

and

U is an ubiquitin ligase binding moiety and is Cereblon (CRBN) E3 ligase moiety having the structure:

((2-(2,6-dioxopiperidin-3-yl)-1,3-dioxoisoindolin-4-yl)amino).

2. A pharmaceutical composition comprising a compound according to claim 1 and a pharmaceutically acceptable carrier, solvent, adjuvant or diluent.

3. A method of treating cancer, wherein the cancer is rhabdomyosarcoma, the method comprising administering to a subject in need of such treatment one or more compounds according to claim 1.

4. The method of claim 3, wherein the rhabdomyosarcoma is fusion positive rhabdomyosarcoma (FP-RMS).

5. A method of ubiquitinating a PAX3-FOX101 fusion protein in a cell, the method comprising administering a compound according claim 1 to the cell.

* * * * *